US006179864B1

(12) United States Patent
Peters-Combs

(10) Patent No.: US 6,179,864 B1
(45) Date of Patent: Jan. 30, 2001

(54) SMOKING CESSATION DEVICE AND METHOD

(76) Inventor: Becky Peters-Combs, 1945 Locust St., Denver, CO (US) 80220

( * ) Notice: Under 35 U.S.C. 154(b), the term of this patent shall be extended for 0 days.

(21) Appl. No.: 09/170,500

(22) Filed: Oct. 13, 1998

Related U.S. Application Data

(60) Provisional application No. 60/064,669, filed on Oct. 13, 1997.

(51) Int. Cl.[7] ..................... A61B 17/00

(52) U.S. Cl. ..................... 606/234

(58) Field of Search ..................... 606/234, 236, 606/235; 131/270, 273, 359, 369; 426/3, 5, 104, 134; 600/240, 239; D1/102, 104, 127

(56) References Cited

U.S. PATENT DOCUMENTS

| | | | | |
|---|---|---|---|---|
| 462,763 | * | 11/1891 | Grabler | 606/235 |
| 2,295,847 | * | 9/1942 | Hume | 606/235 |
| 3,865,115 | * | 2/1975 | De Mieri | 606/235 |
| 4,068,672 | | 1/1978 | Guerra | 131/170 |
| 4,127,125 | * | 11/1978 | Takemoto et al. | 606/42 X |
| 4,269,203 | | 5/1981 | Corbett | 131/270 |
| 4,951,691 | | 8/1990 | Leary | 131/270 |
| 5,284,163 | | 2/1994 | Knudsen et al. | 131/270 |
| 5,284,490 | * | 2/1994 | Green | 606/235 |
| 5,293,883 | | 3/1994 | Edwards | 131/270 |
| 5,308,245 | | 5/1994 | Constantino | 434/236 |
| 5,590,421 | | 1/1997 | Craner | 2/161.7 |
| 5,879,699 | * | 3/1999 | Lerner | 424/440 |

OTHER PUBLICATIONS

Neergaard, Nicotine Inhaler New Way Off Cigarette, The Associated Press.

Seideman, Palomar Direct Sales & Distrubution internet advertisement for Resolve.

Palomar Direct Sales & Distrubution internet advertisement for Resolve.

Blass, et al. Sucrose as an Analgesic for Newborn Infants, Pediatrics.

Campos, Soothing Pain–Elecited Distress in infants with Swaddling and Pacifiers, Child Development, 1989, pp. 781–792.

Gunnar et al., The Effects of a Pacifying Stimulus on Behavioral and Adrenocortical Responses to Circumcision in the Newborn, Journal of the American Acad. of Child Psychiatry, 23, pp. 34–38, 1984.

* cited by examiner

*Primary Examiner*—Michael Buiz
*Assistant Examiner*—Vicki B. Trinh
(74) *Attorney, Agent, or Firm*—Sheridan Ross P.C.

(57) ABSTRACT

A device and method for treating stress-induced habits including smoking, drinking, overeating and the like, is disclosed. The invention consists of an adult pacifier made of a flavored or unflavored resilient material, orthodontically shaped to fit inside the mouth and on the tongue of the user. In moments of stress or when the urge to smoke, overeat, or drink arises, the device is placed on the tongue in the mouth and sucked. This simultaneous suction and tongue undulation, much like the stimulation caused by smoking cigarettes and the like, encourages deep breathing and causes salivation, gastric acid secretion and stimulation of the cranial nerve endings in the tongue.

4 Claims, 12 Drawing Sheets

SMOKING CESSATION DEVICE AND METHOD

RELATED APPLICATION

This application claims priority from U.S. Provisional Patent Application No. 60/064,669, filed Oct. 13, 1997. The entire disclosure of the provisional application is considered to be part of the disclosure of the accompanying application and is hereby incorporated by reference.

FIELD OF INVENTION

The present invention is used to aid in the cessation of the smoking habit. It is designed to take the place of an actual cigarette, allowing sucking, holding something in the mouth, holding something in the hand, the ceremonial hand-to-mouth process, deep breathing and gastric stimulation.

PRIOR ART AND GENERAL BACKGROUND

People who try to stop smoking, overeating, nail biting, thumb sucking and/or drinking try a myriad of programs and products to try to break their addictions. Many people try programs like Smoke Enders, Weight Watchers and Alcoholics Anonymous. Smokers also often try a variety of products including nicotine inhalers, nicotine flavored patches, nicotine flavored gum, artificial cigarettes and/or oral substitutes such as hard candy and gum.

Unfortunately, group programs are often expensive. Nicotine flavored products are often addictive, often causing side effects such as mouth or throat irritation or cough, and are limited in the duration of their usage, and artificial cigarettes so closely emulate the ceremonial hand-to-mouth process that they often fail to make the user stop smoking. Sucking on hard candy can cause weight gain and sucking hard candy and chewing gum can cause tooth decay.

One theory as to why people smoke is that they were weaned too early, that they were not allowed a long enough period to suck, suggesting the continuing need for humans to suck. A straw or an artificial cigarette gives a smoker an object on which to suck but does not activate the same stimulation of chemical responses as the placement of a cigarette or a pacifier in the mouth.

Studies on newborns show that during circumcisions, "stimulation with the pacifier significantly reduced crying" ("The Effects of a Pacifying Stimulus," Gunnar et al., 1984.) According to another study on newborns, "crying and heart rate declined more rapidly in the pacifier condition than in swaddling," (Campos, 1989.) Doctors also found that pacifiers that had been flavored with sucrose were even more effective in calming babies: "Specifically, control infants who underwent a standard circumcision procedure without intervention cried 67% of the time. A water-moistened pacifier reduced crying to 49%. Crying was reduced further by providing infants with a sucrose-flavored pacifier to suck," (Blass, et al, 1991). Sucking on an unflavored pacifier is antinociceptive to infants, and this antinociception is enhanced by sucrose.

Studies on pacification have been restricted to the newborn period and have neglected to address the effectiveness of pacification at older ages. For an adult in our society, sucking on a thumb is a deconditioned activity. Sucking on a cigarette is disdained by the majority, but is allowed. People who smoke, however, develop the habitual need to suck.

There is therefore a need for a smoking cessation device and method that, without the use of addictive drugs, enables a smoker to cease smoking within a reasonable time period. There is a further need for a device for adults that assists them in stopping oral habits such as obsessive eating, nail biting and thumb sucking.

BRIEF DESCRIPTION OF THE FIGURES

FIG. 13D is a side view of the invention with the end of the tongue engaging member filled in.

DETAILED DESCRIPTION OF THE PREFERRED EMBODIMENTS

The present invention 30 fulfills the need for adults to suck and because of the shape, the flavor, the size and the placement in the mouth of the present invention, it fulfills certain chemical responses similar to those created by a cigarette. The adult pacifier 30 allows smokers to suck on a flavored or unflavored resilient pacifier in place of a cigarette, food and/or alcoholic beverage thus encouraging deep breathing, and encouraging stimulating salivation, gastric acid secretion, and the cranial nerve endings of the tongue encouraging deep breathing?.

The adult pacifier of the present invention 30 comprises a unit made up any suitable material such as latex, rubber, silicone, plastic, edible candy sucker material or any material that is FDA approved and can go into the mouth. The material comprising the present device can be flexible or rigid and can be made to have hollow compartments or may be of solid construction. In one embodiment, the tongue can flex the material; in another embodiment, the tongue is unable to flex said material.

In a preferred embodiment, the pacifier is made of a malleable material which molds to the shape of the user's mouth and is constructed of flexible material that is tough enough to be chewed on. The pacifier 30 is able to be shaped and reshaped to fit individual mouths with individual orthodontic considerations.

In another embodiment, the adult pacifier 30 is edible and made of a sugary sucker formula. In still other embodiments, the material is not edible, but is impregnated with a flavor, such as wintergreen, spearmint, cinnamon, almond, bubble gum, watermelon, cherry, apple, lime and the like. For example, the material can be dipped in a flavored oil, or flavored with at least one drop of flavored oil such as wintergreen, spearmint, cinnamon, almond, bubble gum, cherry, apple, lime and the like, preferably a flavor that freshens one's breath or that tastes good.

In one embodiment, the device has a replaceable flavor ampule or cartridge 32 that is provided in the hollow part of the device or in the handle that supports the device. The device can be designed to accept an ampule or cartridge in the hollow part of the device to release various replaceable flavor, medicinal and/or pain reliever packets from the encapsulated part. The adult pacifier can also be soaked or impregnated with a flavored and/or medicated substance (e.g., a nicotine-substitute solution such that it slowly releases a nicotine-substitute solution as it is being sucked).

Figure 20A:
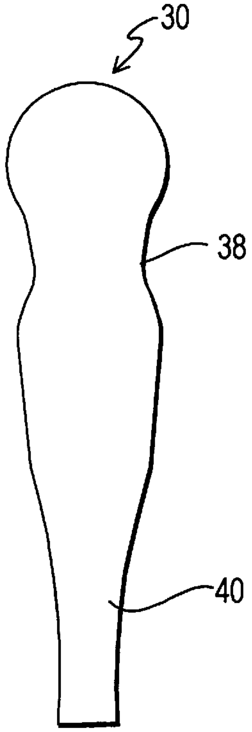
FIGS. 20A–20C depict a tongue engaging member having an integral handle associated therewith.
Figure 20B:
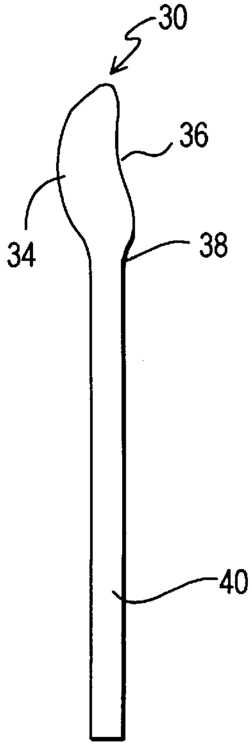
Figure 20C:
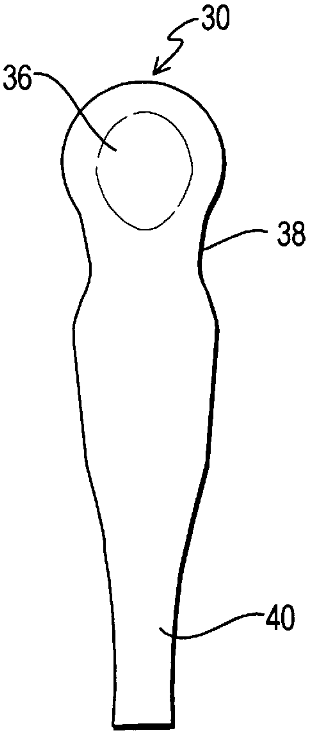

In a preferred configuration the present invention comprises an orthodontically suited hump 34 with a tongue groove 36 on the bottom which contacts with a user's tongue. The groove 36 is preferably of a design such that it allows the tongue to find resistance in the pacifier when the pacifier is being sucked. The hump-shaped part 34 touches the roof of the mouth and the tongue-groove 36 provides tension and resiliency for the tongue. In one embodiment the hump-shaped part 34 of the device has minuscule grooves on the hump shape to match the grooves on the roof of the mouth. A hollow or solid neck 38 is joined to the hump/tooth grove part of the device and fits between the upper and lower teeth. At the end of the neck 38 is a tubular or other shaped handle 40 that is used to extricate the neck and hump/tongue groove from the mouth. These appendages 40 may be a multitude of shapes. They can look like and have the dimensions of cigarettes, cigars, pipe holders, cigarette holders, letters or other suitable designs. In one embodiment, the appendage 40 (whatever shape it is) is made integral (FIG. 1) with the tongue engaging portion of the device 30. Such an appendage may be entirely enclosed in a user's mouth when the lips are closed or it can extend out of the mouth, about the length and width of a cigarette. If an appendage handle 40 is used it is preferably designed to be reversibly insertable into the adult pacifier so that the adult pacifier may be used with or without the cigarette-like appendage (FIG. 2). Other embodiments, however, lack an appendage and/or have the handle 40 integral with the device (e.g., FIG. 20).

Figure 1A:
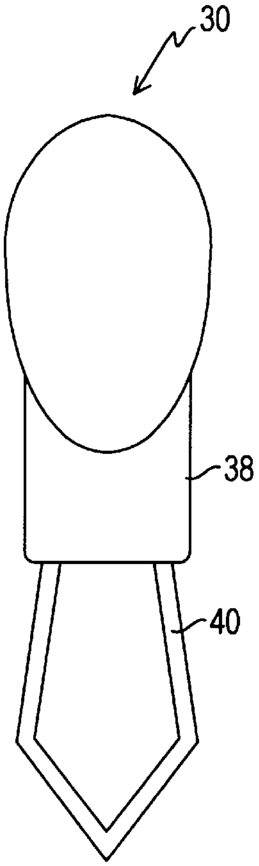
FIGS. 1A–1C show various embodiments of the invention where an appendage is formed integral with the tongue engaging body.
Figure 1B:
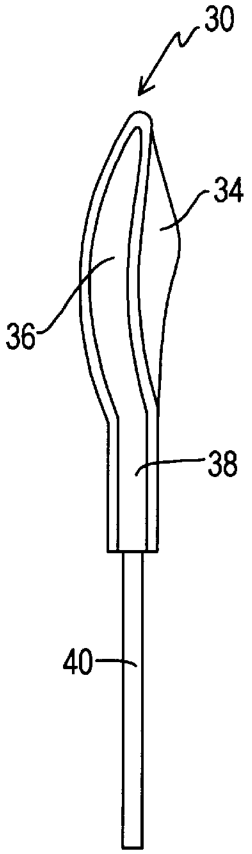
Figure 1C:
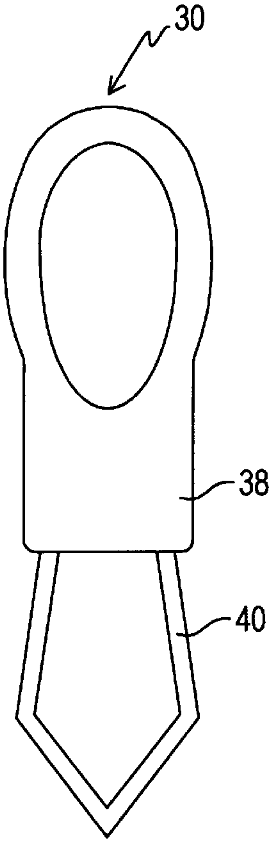
Figure 1D:
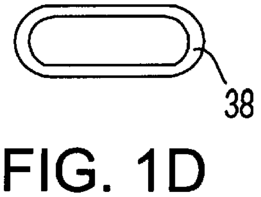
FIG. 1D is a side view of the end of the tongue engaging body.
Figure 2A:
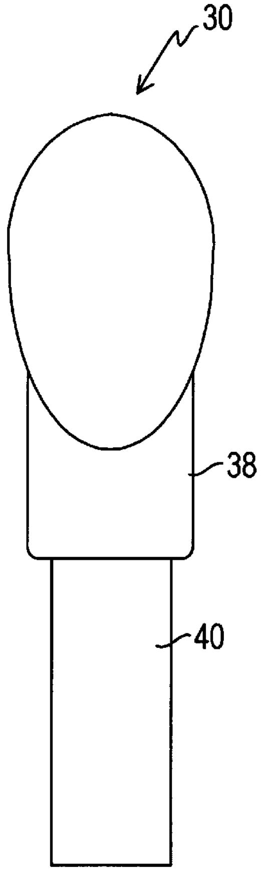
FIGS. 2A–2C show various views of the invention wherein the handle portion is removable from the tongue engaging body.
Figure 2B:
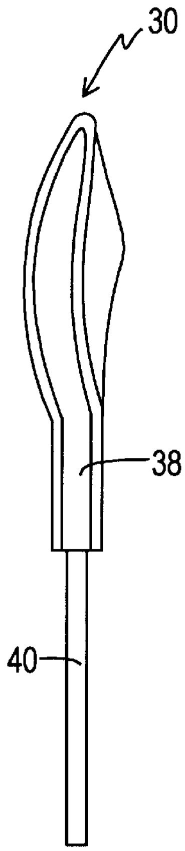
Figure 2C:
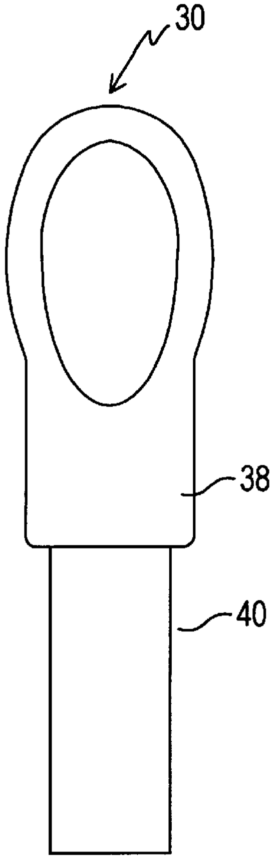
Figure 2D:
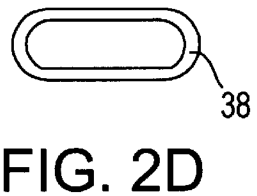
FIG. 2D is a side view of a tubular opening into which the movable appendage is inserted.
Figure 3A:
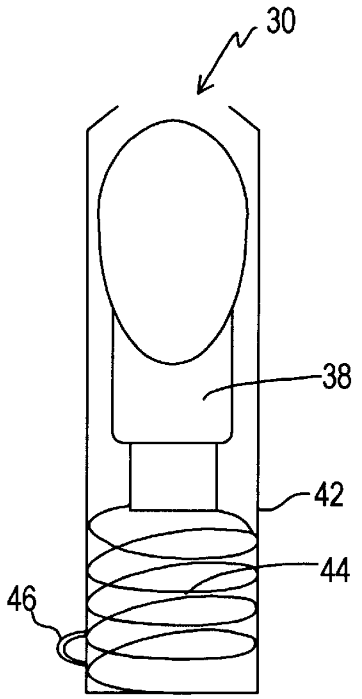
FIGS. 3A–3C are various views of one embodiment of the invention where an elastic mechanism is relied upon to eject the tongue engaging member from the housing.
Figure 3B:
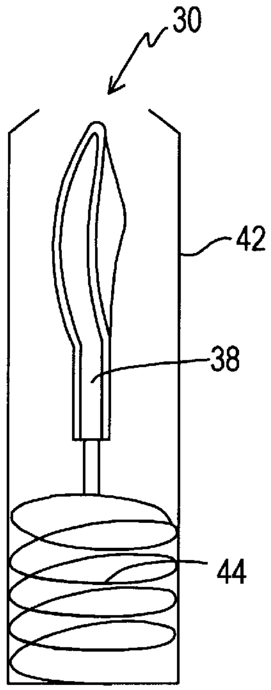
Figure 3C:
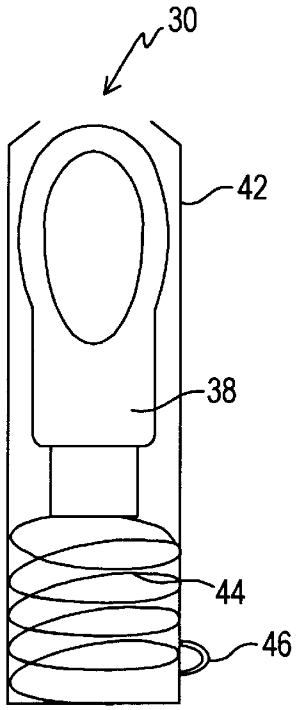
Figure 4A:
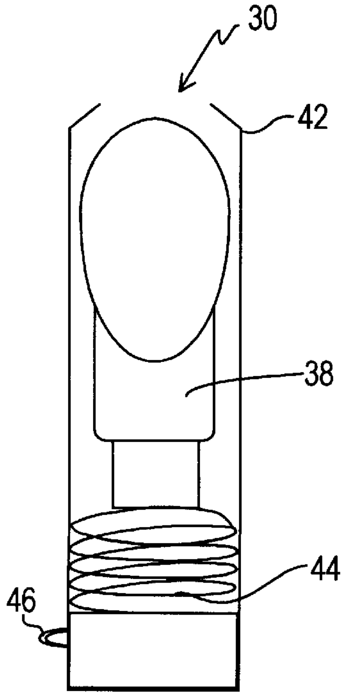
FIGS. 4A–4C depict top, side and bottom views of another embodiment of the invention where the tongue engaging member can be slid out of a housing for engagement with a user's mouth.
Figure 4B:
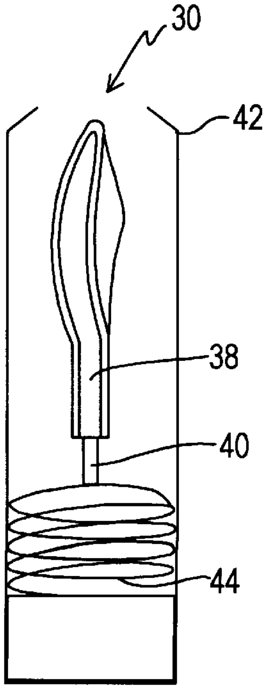
Figure 4C:
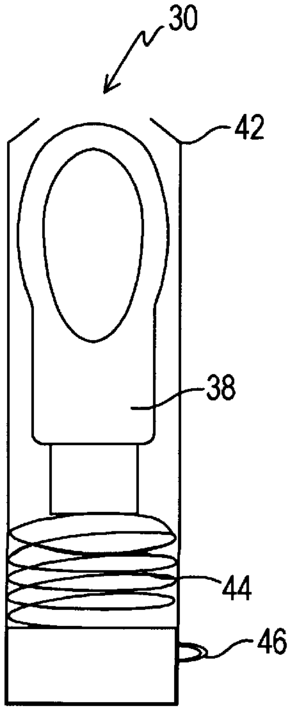

In another embodiment, the device is compressed into a pen-like cartridge 42 and is pushed via a spring mechanism 44 or pushed manually into the user's mouth with the pressing of a button 46 (FIG. 3). The tongue engaging portion can be compressed into a pen-like cartridge 42 and slid into the user's mouth with the sliding of a button 46 on the side of the pen-like cartridge 42 (FIG. 4), operable by a user's tongue.

Figure 5A:
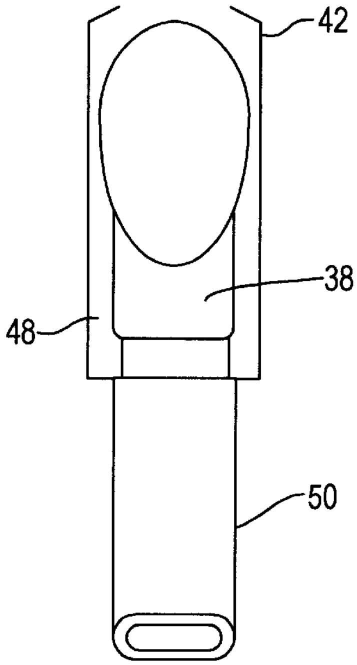
FIGS. 5A–5C show yet another embodiment where the tongue engaging member is reversibly slidable into a housing.
Figure 5B:
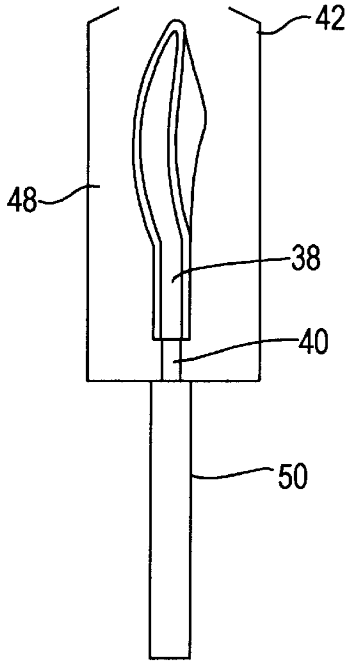
Figure 5C:
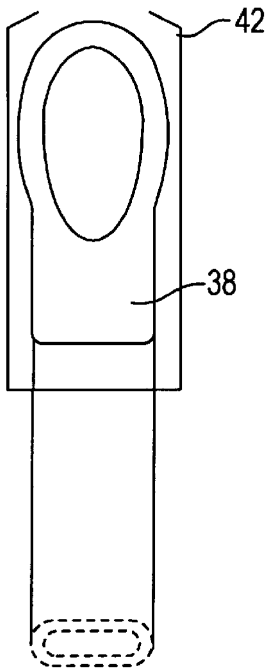

In still another embodiment, the adult pacifier 30 folds into a tube 48 so that it can be pushed out by a smaller 50 tube that is inserted into the bigger tube 48 (FIG. 5) (e.g., a telescoping appendage).

Figure 7A:
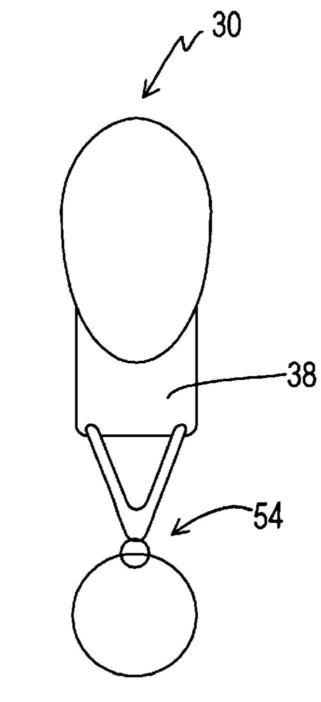
FIGS. 7A–7C show top, side and bottom views of the tongue engaging member connected to an appendage which is itself connected to another component, such as a key ring.
Figure 7B:
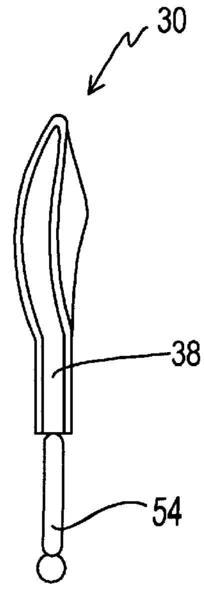
Figure 7C:
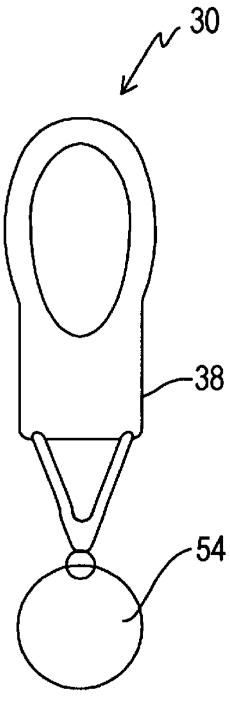
Figure 6C:
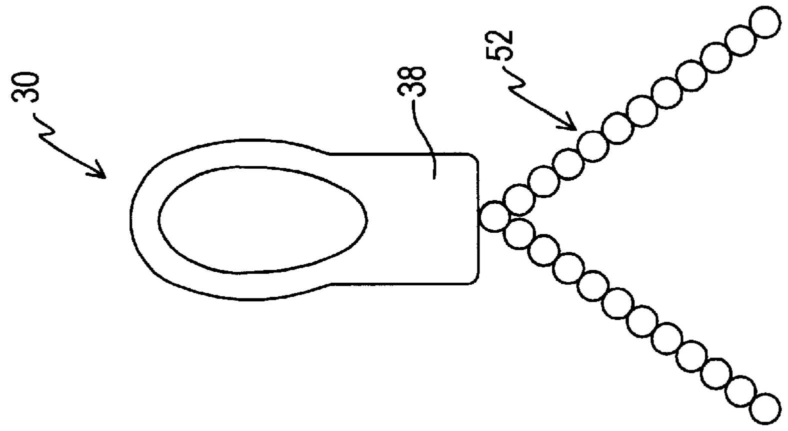
FIGS. 6A–6C show top, side and bottom views of the present invention with the tongue engaging member connected to a neck encircling device.
Figure 6B:
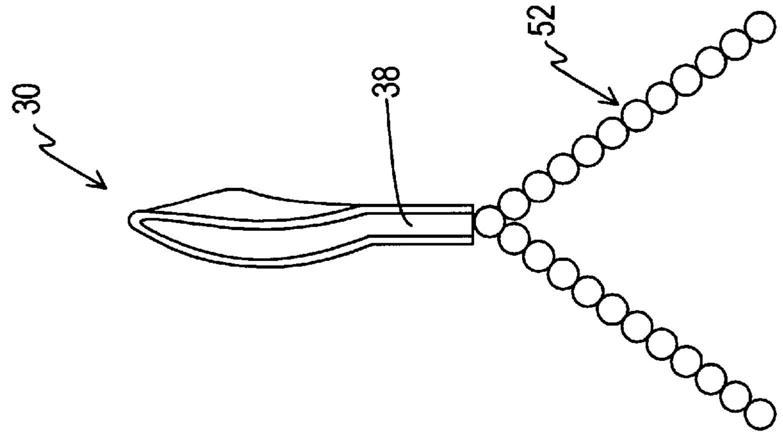
Figure 6A:
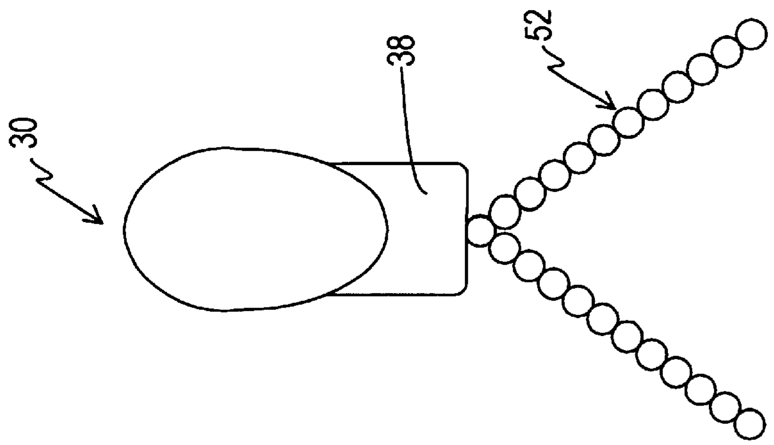
Figure 8A:
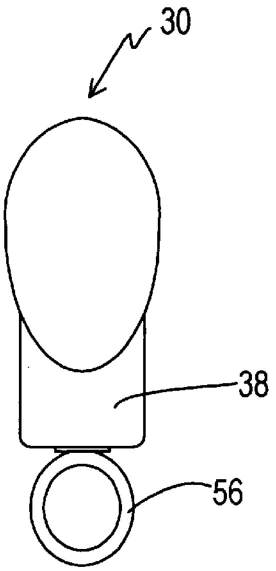
FIGS. 8A–8C depict top, side and bottom views of the tongue engaging member connected to a finger encircling device.
Figure 8B:
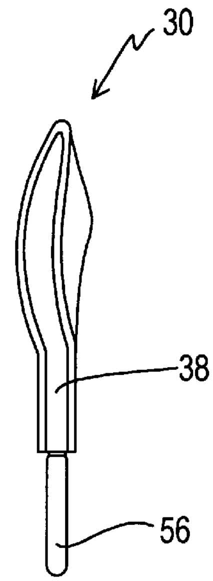
Figure 8C:
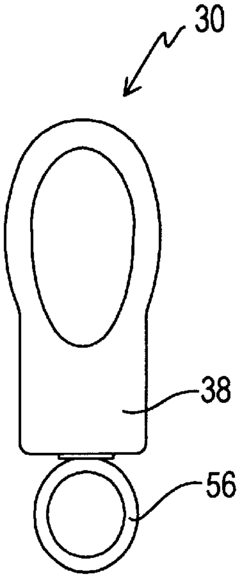
Figure 9A:
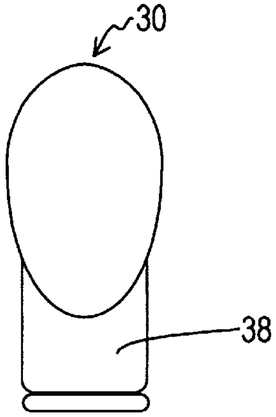
FIGS. 9A–9C show embodiments where the tongue (engaging member can be fitted onto a user's finger or thumb or other article (e.g., pen, pencil, etc.) and then inserted into the user's mouth.
Figure 9B:
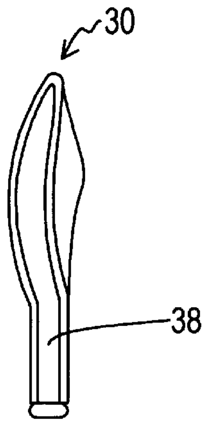
Figure 9C:
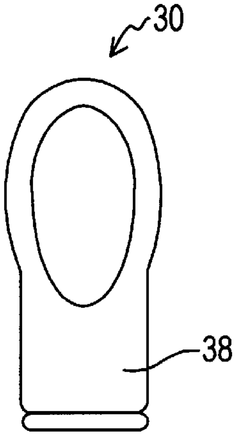

The present invention can be designed so as to hang on a neck-encircling device 52 around a user's neck (FIG. 6). For example, it can hang on a key ring via an appendage (FIG. 7), extend off of a finger-encircling device 56 worn around the user's finger (FIG. 8), and/or be designed to fit on the user's thumb or fingers to be inserted into the mouth (FIG. 9).

Figure 10A:
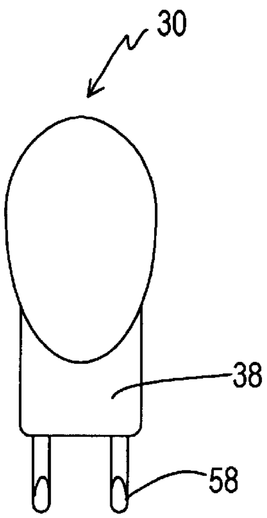
FIGS. 10A–10C show clips that are attached to the tongue engaging member in order to hold the device in a user's mouth by engagement with the user's teeth.
Figure 10B:
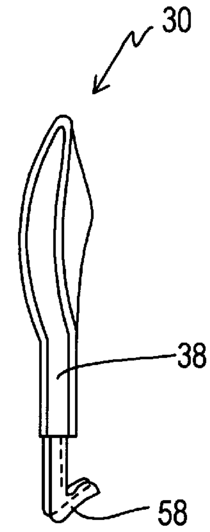
Figure 10C:
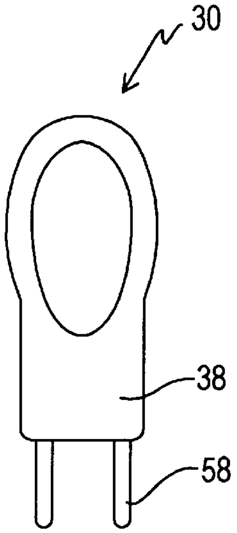
Figure 11A:
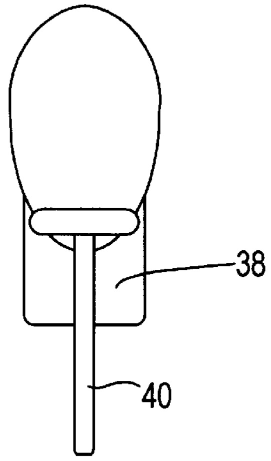
FIGS. 11A–11C show embodiments where a flavor cartridge is used in coordination with the tongue engaging device.
Figure 11B:
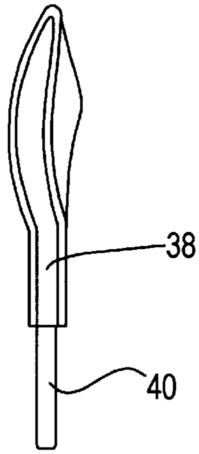
Figure 11C:
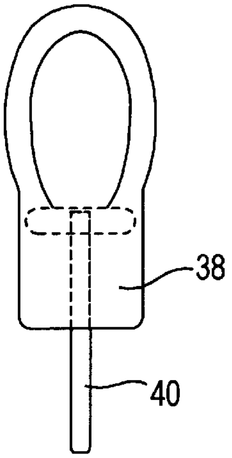

In a further embodiment, the device 30 may comprise edible material and may rest on the user's tongue like a mint. Other designs incorporate the use of a plastic, rubber, or wooden stick 40 (FIG. 2) to support the device and to facilitate manual manipulation of the device. Still other embodiments use one or more clips 58 to hold the device next to a user's teeth (FIG. 10). The appendage itself may contain flavored or medicinal compounds so that when the hump/tongue groove part is sucked on, it releases a flavor and/or medicine to the hump/tongue groove. A cartridge can be inserted into the adult pacifier 30 or a stick 40 can be provided with an ampule attached to the end of it which fits inside the hump-shaped/tongue groove part of the adult pacifier (FIG. 11).

Figure 12A:
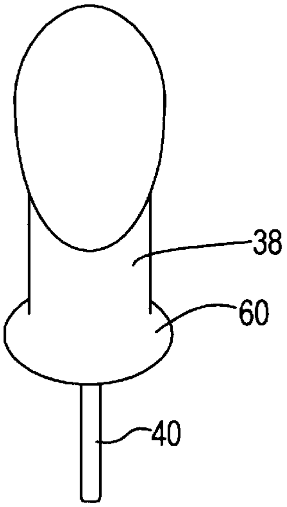
FIGS. 12A–12C depict the tongue engaging member connected to a lip engaging member which is itself connected to a component for manual manipulation by a user.
Figure 12B:
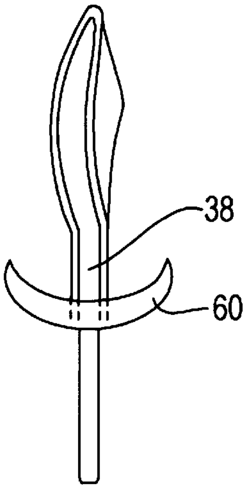
Figure 12C:
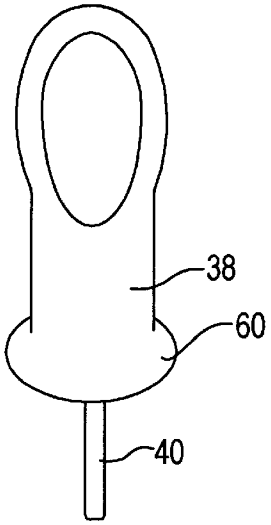
Figure 13A:
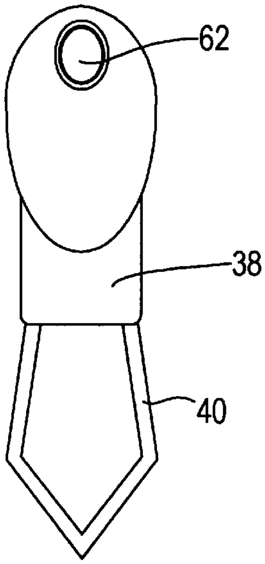
FIGS. 13A–13C depict the tongue engaging member with medical instrumentation devices associated therewith, such as an temperature gauge.
Figure 13B:
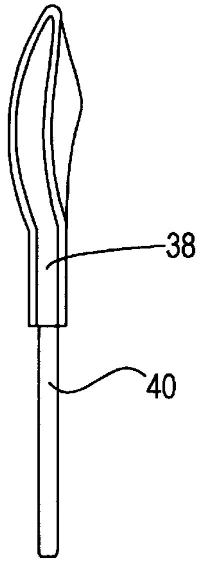
Figure 13C:
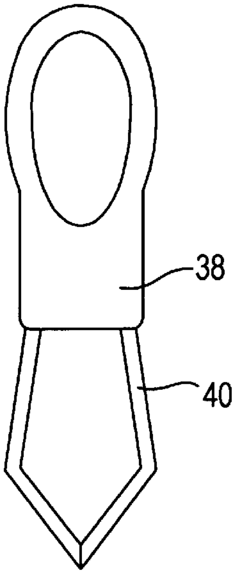
Figure 13D:
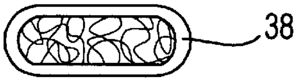
Figure 14A:
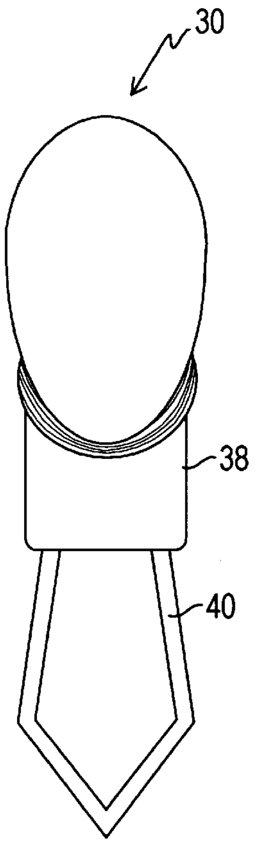
FIGS. 14A–14C depict the tongue engaging member with teeth engaging indentures.
Figure 14B:
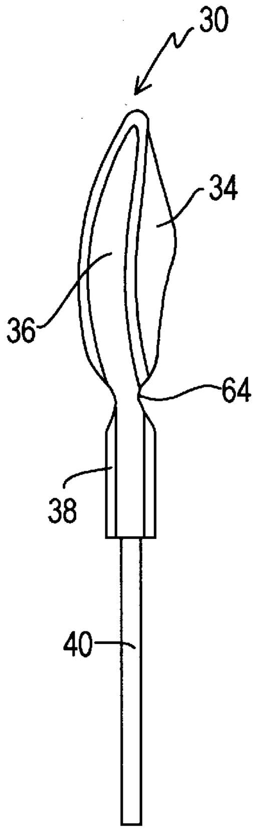
Figure 14C:
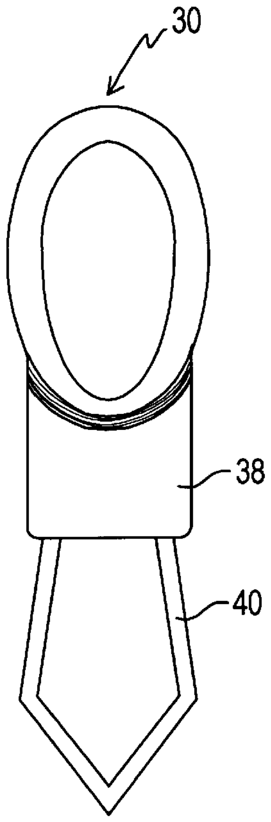
Figure 14D:
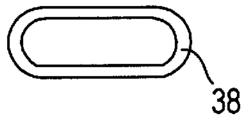
FIG. 14D shows a hollow end of the tongue engaging member through which handles of various sizes and shapes can be inserted.

In one embodiment, the tongue engaging member 30 has a rounded convex or concave plastic end 50 that comfortably rests on the user's lips and is attached to a stick 40 or ring (FIG. 12). The end of the unit can remain hollow or may be plugged with any suitable material, such as natural rubber, silicone, latex, plastic and the like.

In still another embodiment, the hump/tongue groove part of the device 30 can contain small medical instrumentation 62 to, for example, measure temperature, blood pressure, and the like (FIG. 13).

A teeth indentation ditch and/or cavity 64 can also be on the top and/or the bottom sides of the neck portion 38 of the adult pacifier 30 to hold it in place during use. This teeth-engaging device 64 acts to secure the adult pacifier 30 in the mouth while the hump-shaped/tongue groove shape at the back of the mouth (in a hollow embodiment) deflates and returns to its natural shape, depending on the strength of the sucking (FIG. 14).

The adult pacifier 30 must be of a dimension suitable to fit into a user's mouth. Thus, it must be long enough to fit on the user's tongue and preferably it has a length that facilitates a user to easily grasp it so as to insert/remove it from their mouth. The present device can therefore be as long as a cigarette/cigar or alternatively only as long as the user's mouth so as to be entirely concealed when a user's closes his/her lips. It is designed to have a thickness that comfortably rests on the tongue and comfortably fits in the mouth without impairing normal breathing and swallowing functions. In a preferred embodiment, the top of the pacifier is hump-shaped 34 and conforms to the rounded shape of the roof of the mouth. A tongue groove 36 is preferably provided that is recessed and hollow on its bottom side (the part of the pacifier which rests against the tongue) and that provides a surface against which the tongue pushes and presses. Tongue pressure on this part of the adult pacifier causes the bottom of the pacifier to collapse (in hollow embodiments) so that it touches the inside top part of the pacifier. When tongue pressure is lessened, the tongue groove 36 resumes its natural shape and position. When being sucked on, the tongue groove flexes and seemingly inflates and deflates like a small balloon based on the resiliency of the material.

The tongue-groove 36 on the bottom of the device 30 preferably extends from the back of the mouth to right behind the user's teeth. In another embodiment, the tongue-groove 36 extends only half that length from the back of the mouth to the middle of the mouth.

The neck of the device 38 (e.g., the portion nearest the lips when in use) is preferably of a size to fit comfortably in the mouth opening and is big enough in some cases to accept an appendage. The neck of the device can be configured so that it fits comfortably between the teeth and lips. It is preferably constructed of a material that is tough enough that the teeth can grind and chew upon it.

In one embodiment, the adult pacifier 30 simply rests on the user's tongue with the neck 38 only slightly extending outside the user's lips. In another embodiment, it fits inside the user's mouth, simply resting on the user's tongue with the neck resting against the back of the teeth of the user. In yet a further embodiment, the adult pacifier 30 fits comfortably inside the adult user's oral cavity and is attached to both the left and right side by an orthodontic metal clip or clips 58 which engage the unit in the user's mouth by fastening the unit to the user's teeth. In a preferred embodiment, the adult pacifier 30 is long enough to extend past the teeth and past the lips of the user with the hump-shaped part 34 touching the roof of the mouth, and the tongue-groove 36 providing tension and resiliency for the tongue.

Other embodiments relate to the use of a spring mechanism 44 inside a pen-like cartridge 42 so that the tongue engaging member can be reversibly inserted and when retracted, can be easily carried by a user. In one embodiment, the neck end is wide and open enough to fit over the thumb, finger, pen, pencil or similar article of the user, allowing the user to suck on the hump-shaped/tongue groove part while manipulating the tongue on and around the tongue-groove.

One particular aspect of the present invention relates to a method for treating a person's desire to smoke cigarettes, cigars and/or pipes, such method comprising the following steps:

1. Having a user insert into their mouth a tongue engaging member 30 having a substantially curved upper surface 34 and a lower surface 36 with a groove to comfortably conform to a user's tongue;

2. When the desire to smoke arises, having the user suck said member, thereby reducing the user's desire to smoke.

The present method may also include the use of an appendage 40 to be operationally associated with the tongue engaging member 30 to permit a user to reversibly insert and remove the tongue engaging member 30 from their mouth. As described in more detail hereinbelow, the appendage associated with the tongue engaging member 30 can be of any shape or size to facilitate such reversible insertion and removal and in particular, can include a finger encircling member 56, a handle or stick 40, and in particular, can include objects simulating the size and weight and feel of a cigarette/cigar/pipe. A further element of the inventive method includes the simulation of the hand-to-mouth movements associated with normal smoking. As such, the method for using the present device includes the repeated insertion and removal of the tongue engaging member 30 to mimic manipulations of a cigarette/cigar/pipe during a conventional smoking exercise.

In one particular aspect of the present invention, the tongue engaging member 30 that is enclosed within a housing 48 is utilized. The housing can be of a pen-shaped cylinder 48 for concealing with adult pacifier within the housing when not in use. The housing can be connected to the tongue engaging member in a spring-like fashion 44 so that operation of the spring mechanism 44 can act to extend the tongue engaging member outside of the housing 48, thus facilitating a user sucking on the tongue engaging member 30 while holding onto the housing which extends from the lips of the user. The housing can 48 conform and appear as a cigarette, cigar and/or pipe for this purpose.

Another aspect of the present invention relates to the delivery of a desired compound through the use of the present device. For example, the present method includes provision of a flavor, medicine or vitamin formulation impregnated or injected or otherwise brought into contact into the tongue engaging member 30 and/or affiliated therewith (e.g., by an ampule and/or cartridge) so that a user can extract desired amounts of such formulations on a periodic basis and be in some control of such dosage over an extended time period. Various embodiments of the tongue engaging member 30 can be designed having micro pores to facilitate transport of various desired formulations from the interior of the tongue engaging member so that it can be absorbed through the oral cavity of the user.

Another use for the present invention relates to cessation of other undesirable habits such as children that thumb suck, people that suck their tongues, lip suckers and people that suffer from TMJ and various other mouth and jaw maladies. For example, the tongue engaging member 30 can be designed in various configurations to exercise the tongue and jaw in a fashion that provides desirable muscle enhancement to overcome such maladies. Another possible effect of sucking on the present invention is the release of endorphins in the bloodstream. Also the adult pacifier gives the user something to hold and to habitually move to and from the mouth, thus satisfying physical and psychological needs. The present device finds use not only in assisting in cessation of smoking, but also in assisting in termination of undesired oral habits such as nail biting and thumb sucking. It has been found that by using the present device, these and other similar undesired oral habits are ameliorated given the ability to satiate the need for sucking and/or biting an object.

Figure 15A:
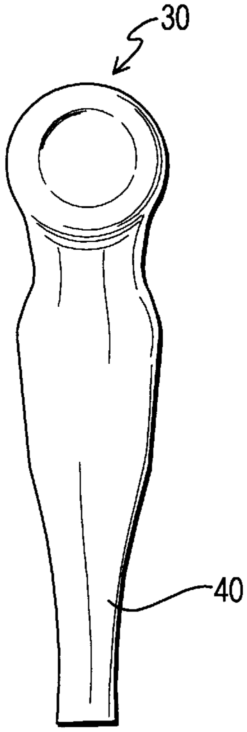
FIGS. 15A–15C depict a tongue engaging member with a "NUK" platform.
Figure 15B:
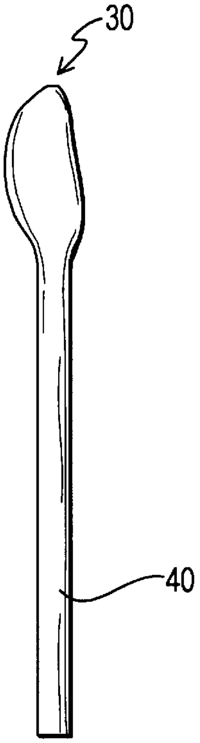
Figure 15C:
Figure 16A:
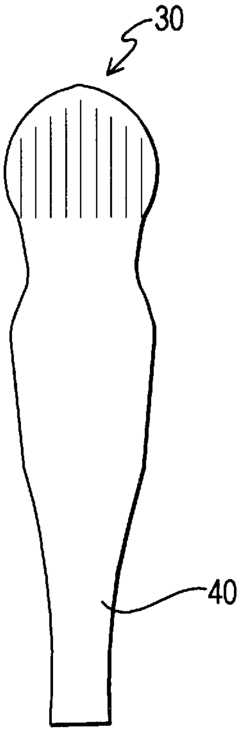
FIGS. 16A–16C depict a tongue engaging member with ridges along at least one side of the member.
Figure 16B:
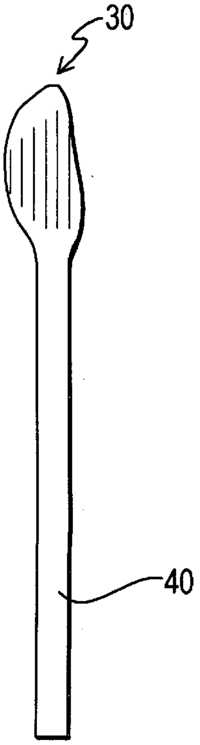
Figure 16C:
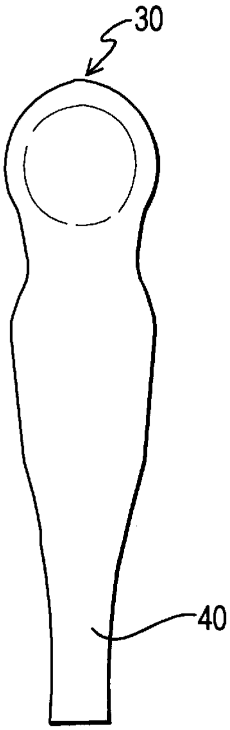
Figure 17A:
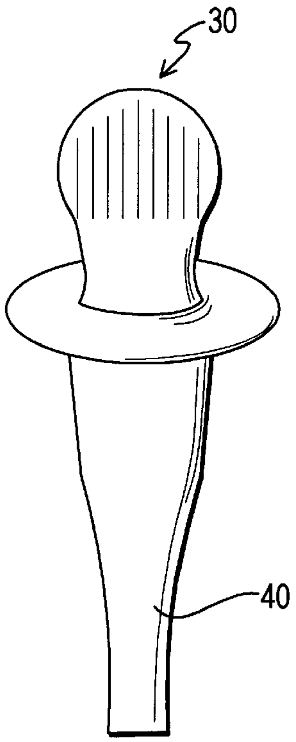
FIGS. 17A–17C depict a tongue engaging member with a mouth guard and/or swallow guard barrier associated therewith.
Figure 17B:
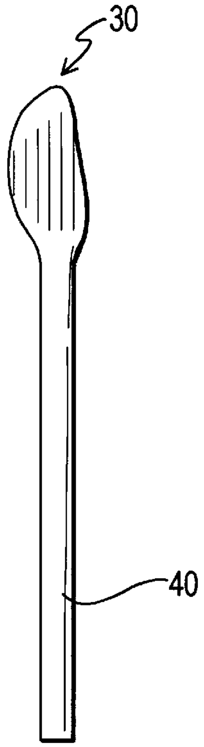
Figure 17C:
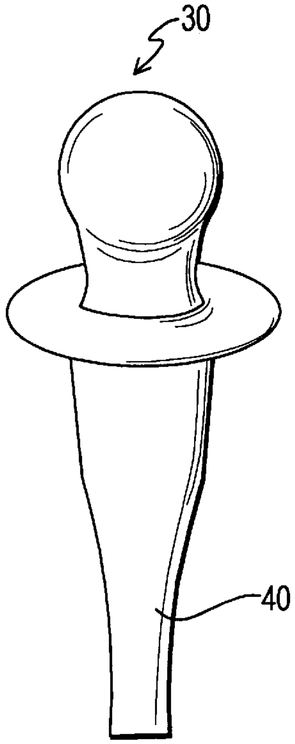
Figure 18A:
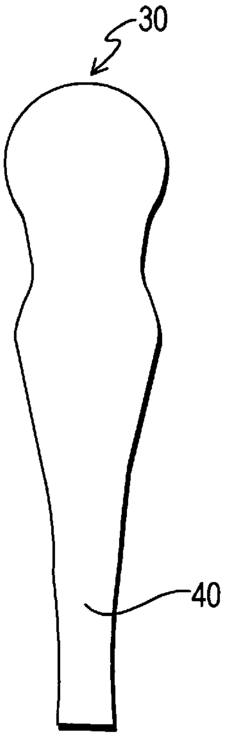
FIGS. 18A–18C depict a balloon shaped tongue engaging member.
Figure 18B:
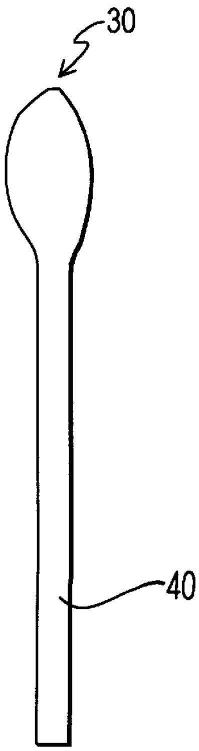
Figure 18C:
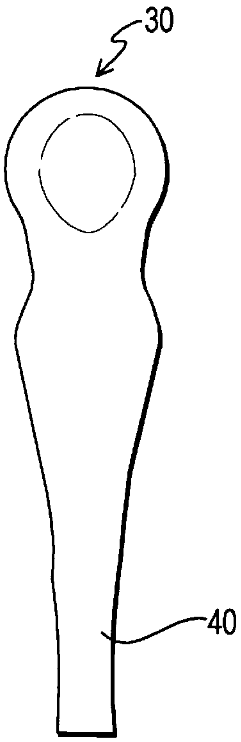
Figure 19A:
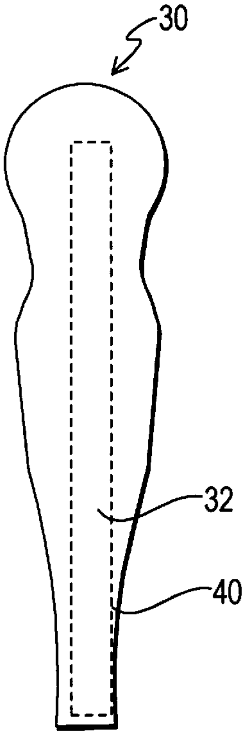
FIG. 19A–19C depict a tongue engaging member having a gel cartridge internally residing therein.
Figure 19B:
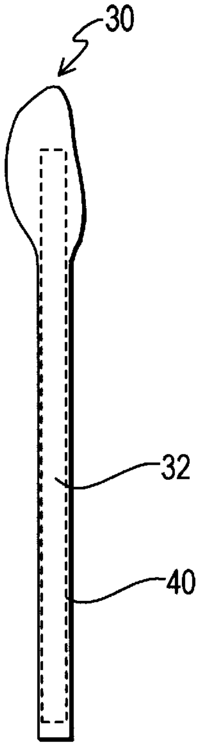
Figure 19C:
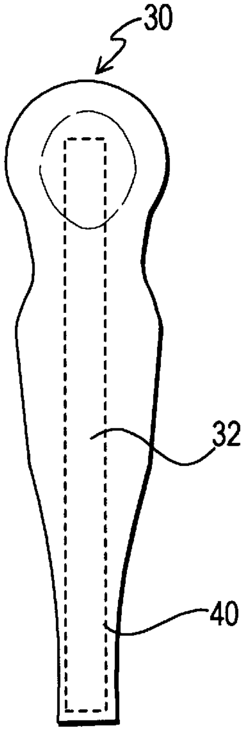

In other embodiments of the present invention, the tongue engaging member 30 can have various shapes (e.g., FIG. 15 with a "NUK" configuration) and/or various textured surfaces such as ridges 66 running either parallel or perpendicular to the direction of a person's tongue (e.g., see FIG. 16). Other embodiments include a mouth guard and/or swallow guard 68 associated with the tongue engaging member (e.g., see FIG. 17) as well as balloon shapes (FIG. 18) and embodiments having a longer integral handle 40 (e.g., FIG. 20) associated with the tongue engaging member 30.

Still other embodiments include cavities within the tongue engaging member 30 to hold a cartridge, such as a gel cartridge, that may contain a flavor packet, a vitamin packet, nicotine, packet, etc. Thus, in various embodiments of the present invention the tongue engaging member 30 may have one or more separate portions or cavities into which various materials can be provided. In one particular embodiment, a gel cartridge 33 is positioned within the tongue engaging member in such a manner that a small hole or friable wall is provided in a partition (not shown) and upon depression of the gel cartridge 32, the gel cartridge 32 material is forced through the aperture/wall into a desired cavity, thus providing the user with an ability to gauge the amount of material coming into contact with the user's tongue. Thus, the present invention provides a device to allow for the slow and/or controlled release of particular formulations at desired rates of administration.

An advantage of the adult pacifier 30 relates to the suction created by the orthodontic shape, and the intensity of the suction affirmed by the resiliency of the material, which combined, produce a soothing effect.

Because many varying and different embodiments may be made within the scope of the inventive concept herein taught, and because many modifications may be made in the embodiments herein detailed in accordance with the descriptive requirements of the law, it is to be understood that the details herein are to be interpreted as illustrative and not in a limiting sense.

What is claimed is:

1. A method for treating an adult person's desire to smoke cigarettes, comprising the following steps:

(a) providing to an adult a pacifier having a hump-shaped portion and a tongue groove portion a size to be put in the adult mouth and to fit on the tongue and to conform to the roof of the mouth, said pacifier comprises of material selected from the group consisting of latex, rubber, silicone and plastic;

(b) when the urge to smoke arises, placing the pacifier in the mouth;

(c) sucking the pacifier and moving the tongue about the tongue-groove portion, causing salivation, gastric acid secretion, and stimulation of the cranial nerve endings in the tongue, in a fashion to the stimulation caused by smoking.

2. The method of claim 1, wherein in step "a" there is included the step of providing the pacifier with a handle selected from the group consisting of a stick hollow tube and finger-encircling member for use in inserting the adult pacifier into the mouth and for use in removing the adult pacifier from the mouth, and for simulating the hand-to-mouth movements associated with smoking.

3. The method as set forth in claim 1, wherein said step of sucking acts to exercise the tongue and jaw of a user in a fashion that provides muscle enhancement.

4. A method for treating an adult person's desire to smoke cigarettes, comprising the following steps:

(a) providing to an adult a pacifier having a hump-shaped portion and a tongue groove portion of a size to be put in the adult mouth and to fit on the tongue and to conform to the roof of the mouth;

(b) when the urge to smoke arises, placing the pacifier in the mouth;

(c) sucking the pacifier and moving the tongue about the tongue-groove, causing salivation, gastric acid secretion, and stimulation of the cranial nerve endings in the tongue, in a fashion to the stimulation caused by smoking, and providing the user with a handle to help simulate the hand-to-mouth smoking ritual;

(d) repeating steps "b" and "c" using the pacifier until the desire to smoke cigarettes is reduced.

* * * * *